United States Patent [19]  [11] 4,182,740
Hartmann et al.  [45] Jan. 8, 1980

[54] FLAME IONIZATION DETECTOR

[75] Inventors: Charles H. Hartmann, Moraga, Calif.; Michael R. Martin, Gastonia, N.C.

[73] Assignee: Varian Associates, Inc., Palo Alto, Calif.

[21] Appl. No.: 820,067

[22] Filed: Jul. 28, 1977

Related U.S. Application Data

[63] Continuation of Ser. No. 662,676, Mar. 1, 1976, abandoned.

[51] Int. Cl.$^2$ ............... G01N 27/62; G01N 31/12
[52] U.S. Cl. ............................... 422/54; 23/232 C
[58] Field of Search ......... 23/254 EF, 254 E, 232 E, 23/232 C; 422/54

[56] References Cited

U.S. PATENT DOCUMENTS

| | | | |
|---|---|---|---|
| 3,086,848 | 4/1963 | Reinecke | 422/54 |
| 3,451,780 | 6/1969 | Prescott et al. | 422/54 |
| 3,502,439 | 3/1970 | Reece et al. | 23/254 EF |
| 3,607,096 | 9/1971 | Hartmann | 23/232 C X |
| 3,661,533 | 5/1972 | David et al. | 23/254 EF |
| 3,814,583 | 6/1974 | Miller et al. | 23/254 EF X |
| 3,920,401 | 11/1975 | Gatiss et al. | 23/254 EF |

Primary Examiner—Joseph Scovronek
Attorney, Agent, or Firm—Stanley Z. Cole; Gerald M. Fisher; John J. Morrissey

[57] ABSTRACT

Dimensionally optimized flame ionization detector for use in chromatography in which positive ions are caused to be collected by applying positive potential to flame tip. It has been discovered that there exists optimum dimensions of the collector electrode and the spacing between collector electrode and flame tip to resist glassing and corrosion without diminishing other operating parameters. The collector electrode inside diameter is in the range of 0.114 inch to 0.3 inch and the flame tip to collector electrode is in range from 1 mm to 3 mm.

4 Claims, 2 Drawing Figures

FLAME IONIZATION DETECTOR

This is a continuation of Ser. No. 662,676 filed Mar. 1, 1976 and now abandoned.

FIELD OF THE INVENTION

This invention is a further development with respect to flame ionization detectors, such as may be used for analyzing organic materials in gas chromatographic applications, automotive exhaust analyses, and breath alcoholic analyses. In particular, this invention is concerned with optimizing the configuration and dimensions of the collector electrode, and the disposition of the collector electrode relative to the flame tip member, so as to provide an optimal flow pattern for the effluent gas through the detector, thereby minimizing corrosion and silicon dioxide contamination.

DESCRIPTION OF THE PRIOR ART

Flame ionization detectors known to the prior art for use in gas chromatographic applications were especially susceptible to contamination by silicon dioxide deposits on their internal surfaces, and to corrosion by hydrochloric acid.

Silicon dioxide contamination results from the combustion in the flame of organic silicon vapors that bleed into the detector from stationary-phase materials in the chromatographic column, and from the passage through the detector of certain deactivation agents as samples to be analyzed or as constituents of such samples. Silicon in the region of the flame was converted to silicon dioxide, which formed glass-like deposits on the internal surfaces of the detector. The silicon dioxide deposits, especially on the collector electrode, tended to interfere with the collection of positive ions indicative of the concentration of particular constituents in the sample gas.

Corrosion was caused chiefly by the presence of chlorine-containing compounds in the sample gas, particularly chlorinated solvent material. In the vicinity of the flame, such chlorine-containing compounds would combine with water vapor to form hydrochloric acid, which tended to condense on internal surfaces of the detector causing corrosion.

SUMMARY OF THE INVENTION

It is an object of this invention to provide optimal configuration and dimensions for the components of a flame ionization detector so as to minimize corrosion and silicon dioxide contamination, while providing the best possible linear range and detectivity for the instrument.

The "linear range" of a detector may be defined as the ratio of the highest concentration of a sample gas constituent for which the detector will yield a linear response to the lowest such concentration detectable. The "detectivity" of a detector is defined as the ratio of two times the background noise level of the instrument to the sensitivity of the instrument. Detectivity is a parameter used to indicate the smallest quantity of the sample gas constituent of interest that can be definitively detected.

Linear range and detectivity are, as a practical matter, empirically determined functions of the configuration and of the dimensions of the components of a detector. The practicability of fabricating certain components in particular dimensions often depends upon an appropriate choice of materials to accommodate such dimensions.

In accordance with a principal object of this invention, the gaseous effluent from a chromatographic column is mixed with a fuel gas such as hydrogen, and the mixture is passed through a conduit structure that terminates in a flame tip member. The flame tip member is disposed within a region into which an oxidizing gas such as oxygen or purified air is passed. A means is provided for igniting the mixture of fuel and effluent gases in the oxidizing gas, so as to maintain a flame at the flame tip member. A positive electrical potential is applied to the flame tip member, thereby creating an electric field pattern that causes positive ions produced in the ionizing flame to migrate to a collector electrode. The free electrons and negative ions produced in the flame are attracted to the flame tip member. The collector electrode, according to this invention, is a hollow cylindrical structure disposed coaxially with respect to the flame tip member, but is spaced apart from the flame tip member by an axial distance of from 1 to 3 millimeters. In operation, for a given flow rate of the mixture of fuel and effluent gases, the height of the flame varies more or less monotonically with the concentration of ionizable constituents in the effluent. For relatively large concentrations of ionizable constituents in the effluent, the flame is large enough to enter the interior of the collector electrode.

The application of a positive electrical potential to the flame tip member is the usual mode of operation envisioned for the detector of this invention. However, for dual channel chromatography, it would be desirable to apply a positive potential to the flame tip member of one detector and a negative potential to the flame tip member of the other detector. The positive potential would be applied to the analysis channel detector, and the negative potential would be applied to the reference channel detector, so that the signal produced on the reference channel would null any background from the analysis channel.

Both the dynamic range and the linear range of the detector have been found to be optimal, if the positive potential applied to the flame tip member is about 285 volts dc. Experiments show that for such a potential, the linear range of the flame ionization detector, configured as described above, is optimized when the inside diameter of the collector electrode has a value between 0.114 inch and 0.234 inch, where these measurements are believed to be significant to about the second decimal place. It has also been determined that contamination and corrosion are minimized when the inside diameter of the collector electrode is 0.23 inch, where this measurement is significant to the first decimal place. As a matter of expediency in the fabrication of such a collector, an inside diameter of from two-tenths to one-quarter inch may be considered optimum.

With respect to the minimization of contamination and corrosion, an overall length of approximately 1 inch for the collector electrode has been found to be optimal. It is recognized that a collector electrode of smaller length would present a smaller surface area for exposure to contamination and corrosion. However, it has been found that for collector electrode lengths much shorter than 1 inch, the linearity of response cannot be maintained.

The collector electrode according to this invention is mounted within the detector in such a way that the effluent gas and the combustion and ionization products after leaving the vicinity of the flame, must exit from the detector along a single flow path, with the interior of the collector electrode compressing a portion of the exit flow path. The collector electrode is thermally insulated to remain hot as the result of the passage of the combustion products therethrough, thereby inhibiting the deposition of contaminants thereon.

DESCRIPTION OF THE PREFERRED EMBODIMENT

Figure 1:
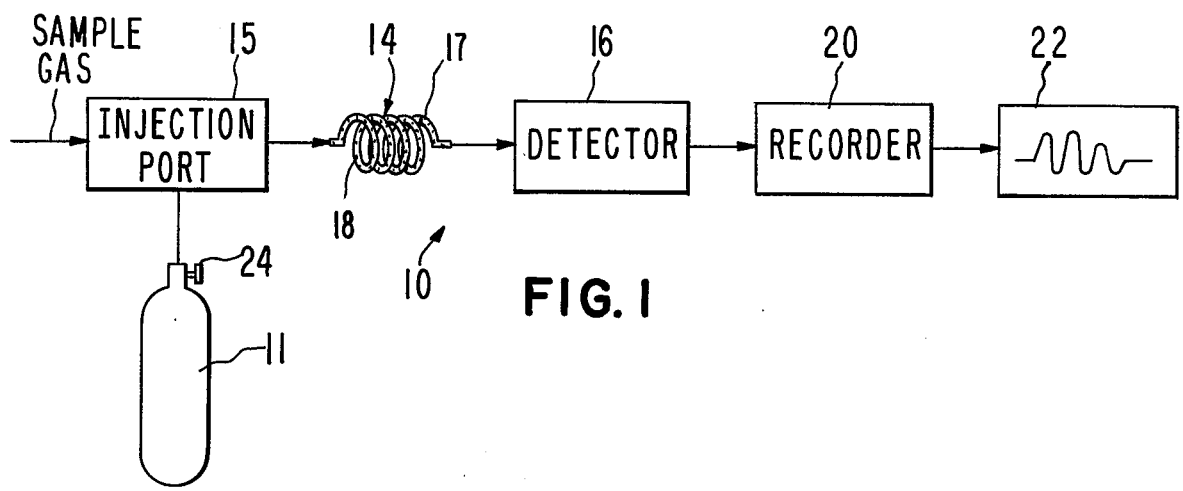
FIG. 1 is a diagrammatic view showing a gas chromatographic system incorporating the flame ionization detector of this invention.

FIG. 1 shows a gas chromatographic system, which incorporates the flame ionization detector of this invention. The gas chromatographic system 10 provides information as to the amount and nature of the components of an unknown sample gas.

The system 10 includes a pressurized container 11 for storing a supply of carrier gas, such as nitrogen. The container 11 delivers a stream of carrier gas to a chromatographic column 14. A quantity of sample gas is added to the carrier gas stream via an injection port 15 located in a conduit between the container 11 and the column 14. Stationary phase material within the column 14 adsorbs some or all of the constituents of the sample gas in varying degrees, such that the effluent from the column 14 exhibits a particular measurable property that is a time-varying function of the nature and amount of the constituents of the sample gas. A detector 16 senses variations in this measurable property of the effluent, and actuates a recorder 20 for providing a permanent record 22 of the time variations of this measurable property. The carrier gas supply container 11 may also include a variable restriction 24, such as a needle valve or a flow controller, for adjusting the rate of flow of the carrier gas toward the colunn 14.

The injection port 15 may comprise any suitable type of device known to those skilled in the art for injecting the sample gas into the high-pressure carrier gas stream flowing between the carrier supply container 11 and the column 14.

The column 14 likewise may be of a type known to those skilled in the art, and comprises an elongate tubular portion 17 containing a stationary phase material 18. The mixture of carrier gas and sample gas percolates through the stationary phase 18 within the tubular portion 17. The stationary phase 18 is a liquid or solid material chosen for its property of differentially adsorbing certain substances, preferably the anticipated constituents of the sample gas. By reason of such differential adsorption, at least one property of the effluent from the column 14 is caused to vary as a function of time, the time function being related to the capability of the stationary phase 18 to adsorb constituents of the sample gas.

If the effluent from the column 14 is passed through a detector 16 having an ionizing flame, and if the positive ions generated in the ionization process are caused to migrate to a collector electrode under the influence of an electric field, time variations in the ionization of the effluent can be indicated by measuring the positive ion current to the collector electrode. Such time variations in the ionization of the effluent can be recorded by a recorder 20 connected by suitable electronic circuitry to the detector 16. The recorder 20, which is preferably a strip chart recorder, produces a permanent recording 22 indicating the time variations in the ionization of the effluent.

Figure 2:
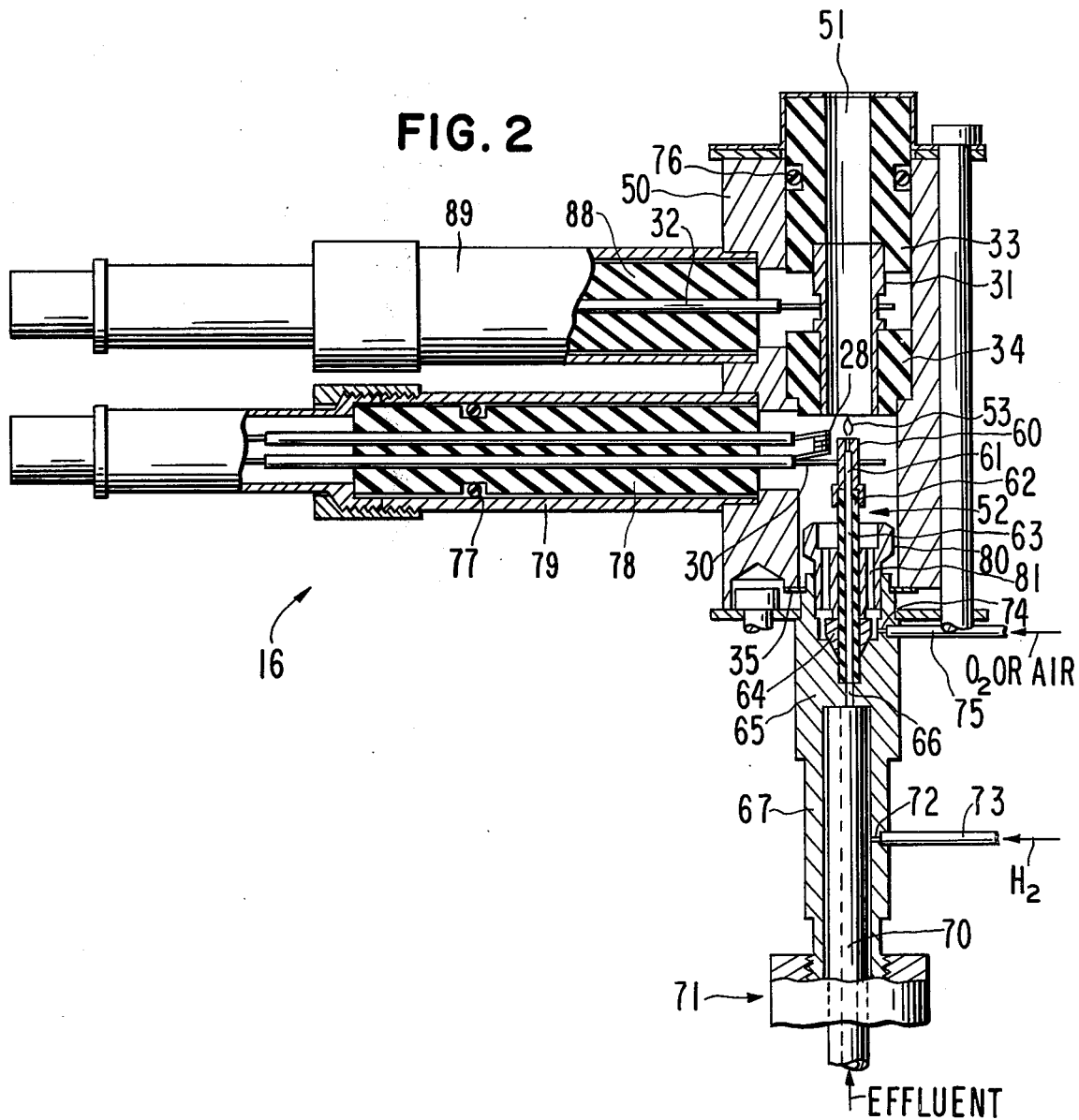
FIG. 2 is an elevational view, showing the inventive portions of the system of FIG. 1 in cross-section.

FIG. 2 illustrates in detail the flame ionization detector of this invention. The detector 16 comprises a tubular housing structure 50 made of a rigid material, such as brass or stainless steel, that is relatively heat and corrosion resistant. A flow passage 51 for gaseous material runs axially through the housing structure 50.

A gas jet structure, generally indicated by the reference number 52, is positioned in the flow passage 51 for producing an ionizing flame 53. The gas jet structure 52 comprises a cylindrical flame tip member 60 having a central bore 61. The flame tip member 60 is made of an electrically conductive metal such as Kovar metal, and is mechanically coupled to an electrically insulating support member 62 having a central bore 63 that is in open communication with the central bore 61 of the flame tip member 60. In the preferred embodiment illustrated in FIG. 2, the flame tip member 60 and the insulating support member 62 are coaxially aligned cylindrical structures, with one end of the support member 62 being received within an adjacent end of the flame tip member 60. The support member 62 is preferably made of an electrically nonconductive ceramic material, which allows the flame tip member 60 to be electrically biased independently of whatever electrical potential may be on the housing structure 50 or on the other metal components of the detector.

The ceramic support member 62 is swage-locked by a compression ferrule 64 into one end of a generally cylindrical metallic base member 65 that closes one end of the housing structure 50. The other end of the housing structure 50 is open to atmosphere or (as would be necessary in the case of a toxic effluent gas) may communicate with effluent receiving means not shown. The base member 65 likewise comprises a hollow cylindrical structure, whose central bore 66 is coaxially aligned with the central bores 63 and 61 respectively of the insulating support member 62 and of the conducting flame tip member 60.

The other end of the base member 65 is configured to receive a feed tube 70 bearing effluent from a gas chromatographic apparatus. The feed tube 70 is received within a cylindrically overlapping portion 67 of the base member 65, where the inside diameter of the cylindrically overlapping portion 67 is slightly larger than the outside diameter of the feed tube 70. The extremity of the overlapping portion 67 is crimped against the surrounded feed tube 70 by any standard technique, such as by nut and ferrule means as indicated by reference number 71. The function of the nut and ferrule means 71 is to achieve a gas-tight seal.

An entry port 72 through the overlapping portion 67 of the base member 65 receives a feed tube 73 bearing a fuel gas, such as hydrogen, from a regulated supply not shown. The fuel gas enters through the entry port 72 into the region between the feed tube 70 and the overlapping portion 67 of the base member 65, and passes thence to the central bore 66 where the fuel gas is mixed with the effluent gas from the feed tube 70. The mixture of fuel and effluent gases then passes through the central bores 63 and 61 into the region immediately outside the flame tip member 60.

An entry port 74 through the base member 65 receives a feed tube 75 bearing an oxidizing gas, such as oxygen or purefied air, from a regulated supply not shown. The oxidizing gas enters through the entry port 74 into a region within the base member 65 external to the insulating support member 62 and the swage-locking compression ferrule 64. A nut 80 is received within that extremity of the end of the base member 65 in which the insulating support member 62 is received. The nut 80 secures the insulating support member 62 in coaxial disposition with respect to the tubular housing structure 50. Channel means 81 through the nut 80 provides a passageway for the oxidizing gas from the entry port 74 to the region within the flow passage 51 immediately surrounding the jet structure 52.

An igniter coil 28 disposed adjacent the flame tip member 60 serves to ignite the mixture of fuel and effluent gases, in the presence of the oxidizing gas, when a difference of electrical potential is applied across the coil 28. As the fuel gas is oxidized, the flame 53 is produced. The flame 53 ionizes any organic constituents in the effluent gas.

A positive dc potential of about 285 volts is applied to the flame tip member 60 by an electrically conductive spring clip lead 30. A generally cylindrical collector electrode 31 is supported within the flow passage 51 so as to be coaxially aligned with but spaced apart from the jet structure 52. In operation, for a given flow rate of the mixture of fuel and effluent gases, the height of the flame 53 varies monotonically with the concentration of ionizable constituents in the effluent. For large concentrations of ionizable constituents in the effluent, the flame 53 may become quite large. With the detector being operated so that the jet structure 52 is in the vertical position, the flame 53 may rise high enough to enter within the interior of the cylindrical collector electrode 31. Regardless of whether or not the flame 53 is actually within the interior of the collector electrode 31, nevertheless the closest metallic structure (and the closest structure of any kind) with which positive ions generated by the ionization process can come into contact is the inner surface of the collector electrode 31.

An electrometer means (not shown) is connected to the collector electrode 31 by an electrically conductive lead 32. The electrometer means is connected to ground and provides a current signal that is quantitatively indicative of the extent of ionization occurring in the flame. The difference of potential between the substantially grounded collector electrode 31 and the flame tip member 60 causes positive ions created in the region of the flame 53 to migrate to the collector electrode 31. The collector electrode 31 is long enough to insure that substantially all positive ions produced by the ionization process are collected on the interior surface thereof. Thus, the electrometer signal can be utilized to indicate the concentration of ionizable constituents in the effluent from a chromatographic column.

The collector electrode 31 is supported in place in the flow passage 51 by means of thermally and electrically insulating sleeve structures 33 and 34, which fit tightly between the outer surface of the collector electrode 31 and the inner surface of the tubular housing structure 50. The sleeve structures 33 and 34 are made of a ceramic material such as aluminum oxide or boron nitride. A high degree of thermal isolation is desirable for the collector electrode 31 in order that the collector electrode 31 can operate as hot as possible so as to inhibit the deposition of other contaminants thereon.

The only flow path for gases out of the region around the jet structure 52 is through the flow passage 51. The base member 65, which closes one end (i.e., the "hot" end) of the housing structure 50, bears against one side of an aluminum washer 35, while the housing structure 50 itself bears against the other side of the same aluminum washer 35, thereby forming a gas-tight seal. Near the other end (i.e., the "cool" end) of the housing structure 50, a silicone O-ring 76 provides a gas-tight seal between the inner wall of the housing structure 50 and the sleeve structure 33. The electrical lead 30 to the flame tip structure 60, and the electrical leads to the heater coil 28, are supported within an insulating structure 78, which in turn is encased in a surrounding outer metal casing 79. Similarly, the electrical lead 32 from the collector electrode 31 to the electrometer is supported within an insulating sleeve 88, which in turn is likewise encased in an outer metal casing 89. Within both outer metal casings 79 and 89, O-rings, such as O-ring 77 shown between the outer casing 79 and the insulating structure 78, provide gas-tight seals to prevent gas leakage through the electrical lead casings.

The salient features of this invention lie in the dimensions of the collector electrode 31, and in the disposition of the collector electrode 31 with respect to the flame tip member 60. It has been determined that the linear range of the detector is optimized when the inside diameter of the collector electrode 31 is between 0.114 inch and 0.234 inch. These measurements are believed to be significant to the second decimal place. It has also been determined that silicon dioxide contamination and corrosion are minimized when the inside diameter of the collector electrode 31 is 0.23 inch. This measurement is believed to be significant to the first decimal place. Consequently, as a matter of expediency in the fabrication of collector electrode elements, the inside diameter of the collector electrode 31 should be less than 0.30 inch, preferably between 0.20 and 0.25 inch.

With respect to the minimization of contamination and corrosion, an overall length of 1 inch for the collector electrode 31 has been determined to be optimum.

The axial positioning of the collector electrode 31 with respect to the flame tip member 60 has also been found to have an important effect on the amount of contamination and corrosion experienced by the collector electrode 31. The most advantageous trade-off between response linearity of the detector on the one hand and the amount of contamination and corrosion that can be tolerated on the other hand occurs when the collector electrode 31 is spaced apart from the flame tip member 60 by approximately 1 millimeter. However, such close spacing has been found to cause the flow of gas into the interior of the collector electrode 31 to be so rapid as to make ignition of the flame a difficult matter. Consequently, for commercial applications it has been found necessary to provide a greater distance between the collector electrode 31 and the flame tip member 60. Considering the practical requirement of trouble-free ignition of the flame, the optimal spacing of the collector electrode 31 from the flame tip member 60 has been found to be 3 millimeters.

The above-disclosed optimal dimensions for the collector electrode, and for the positioning of the collector electrode relative to the flame tip member, provide for rapid and turbulent passage of the gases and ionization products out of the interior of the collector electrode. This rapid and turbulent passage of the gases and ionization products, in conjunction with the insulatedly hot walls of the collector electrode, minimizes the opportunity for silicon dioxide deposits and for hydrochloric acid condensation to form on the surface of the collector electrode. It has been found that these dimensions, in practice, virtually eliminate the silicon dioxide contamination and the hydrochloric acid corrosion that plagued flame ionization detectors of the prior art.

The flame ionization detector of this invention, by reason of the optimization of the dimensions of the collector electrode and of the spacing of the collector electrode with respect to the flame, provides excellent linearity of response and excellent dynamic range with minimal silicon dioxide contamination and hydrochloric acid corrosion. At operating temperatures above 100° C., the linearity of response and the dynamic range of the detector of this invention are superior to what could be achieved with flame ionization detectors known to the prior art.

What is claimed is:

1. A flame ionization detector comprising a flame tip member; means for providing a fuel gas and an oxidizing gas to the vicinity of said flame tip member so that, in operation, a flame can be maintained adjacent said flame tip member; means for introducing a sample gas to said flame; a generally cylindrical collector electrode; and means for maintaining an electrical potential for collecting on said collector electrode positive ions generated by ionization of said sample gas in said flame; said flame tip member being disposed coaxially with respect to and axially spaced apart from one end of said collector electrode so that the spacing between said flame tip member and the bottom edge of said collector electrode is in the range from 1 millimeter to 3 millimeter displaced; the inside diameter of said collector electrode being in the range from 0.114 inch to 0.3 inches.

2. The flame ionization detector of claim 1 wherein the axial length of said collector electrode is not greater than one inch.

3. The flame ionization detector of claim 1 wherein the inside diameter of said collector electrode is in the range from 0.20 inch to 0.25 inch, and the spacing between said flame tip member and said collector electrode in operation is approximately 3 millimeters.

4. The flame ionization detector of claim 1 wherein said means for maintaining an electrical potential for collecting positive ions on said collector electrode comprises means for applying a positive electrical potential to said flame tip relative to the electrical potential of said collector electrode.

* * * * *